United States Patent

Sherman et al.

[11] Patent Number: 5,750,404
[45] Date of Patent: May 12, 1998

[54] REAGENT FOR THE DETERMINATION OF WATER AMD ENE-DIOLS OR THIOLS

[76] Inventors: Felix Sherman, 34/5 Yizhak Tuniq Street, Jerusalem 97795; Ilya Kuselman, 29/5 Haim Pazner Street, Jerusalem 97552; Avinoam Shenbar, 4 Tiltan Street, Jerusalem 96920, all of Israel

[21] Appl. No.: 695,900

[22] Filed: Aug. 12, 1996

[30] Foreign Application Priority Data

Aug. 15, 1995 [IL] Israel ........................ 114938

[51] Int. Cl.$^6$ ........................................ G01N 33/18
[52] U.S. Cl. ............................................... 436/42
[58] Field of Search ........................... 422/61; 436/39–42

[56] References Cited

U.S. PATENT DOCUMENTS

| | | | |
|---|---|---|---|
| 4,740,471 | 4/1988 | Scholz | 436/42 |
| 4,874,709 | 10/1989 | Fischer et al. | 436/42 |
| 5,179,024 | 1/1993 | Dahms | 436/42 |
| 5,340,541 | 8/1994 | Jackson et al. | 436/42 |
| 5,466,606 | 11/1995 | Scholz | 436/42 |
| 5,567,618 | 10/1996 | Scholz | 436/42 |

OTHER PUBLICATIONS

Sherman, F. et al. Talanta, vol. 43 (Jul., 1996), pp. 1035–1042.

Primary Examiner—Jeffrey Snay
Attorney, Agent, or Firm—Edwin D. Schindler

[57] ABSTRACT

Novel reagents and the rapid technique were developed for the simultaneous determination of water and ene-diols or thiols in chemical products, drugs and other materials which are inaccessible for direct K. Fischer titration. The reagents include iodine, tetramethylammonium iodide or potassium iodide, non-toxic organic or inorganic base adapted to provide a pH in range of 5.5 to approximately 8.0 (diethanolamine, thriethanolamine, sodium acetate or/and urea) in methanol or another alcohol mixed with N,N-dimethyl-formamide, or with formamide, or with dimethyl sulfoxide and N,N dimethylformamide mixture as a solvent. The use of the reagents is based on the consecutive titration first a) of an ene-diol or thiol by the novel reagents and then b) of water by a conventional K. Fischer reagent in the same cell in a system protected from water vapour and oxygen, with the help of the double burette for electrometric location of the end point in both titrations (or a multistage titroprocessor).

6 Claims, 1 Drawing Sheet

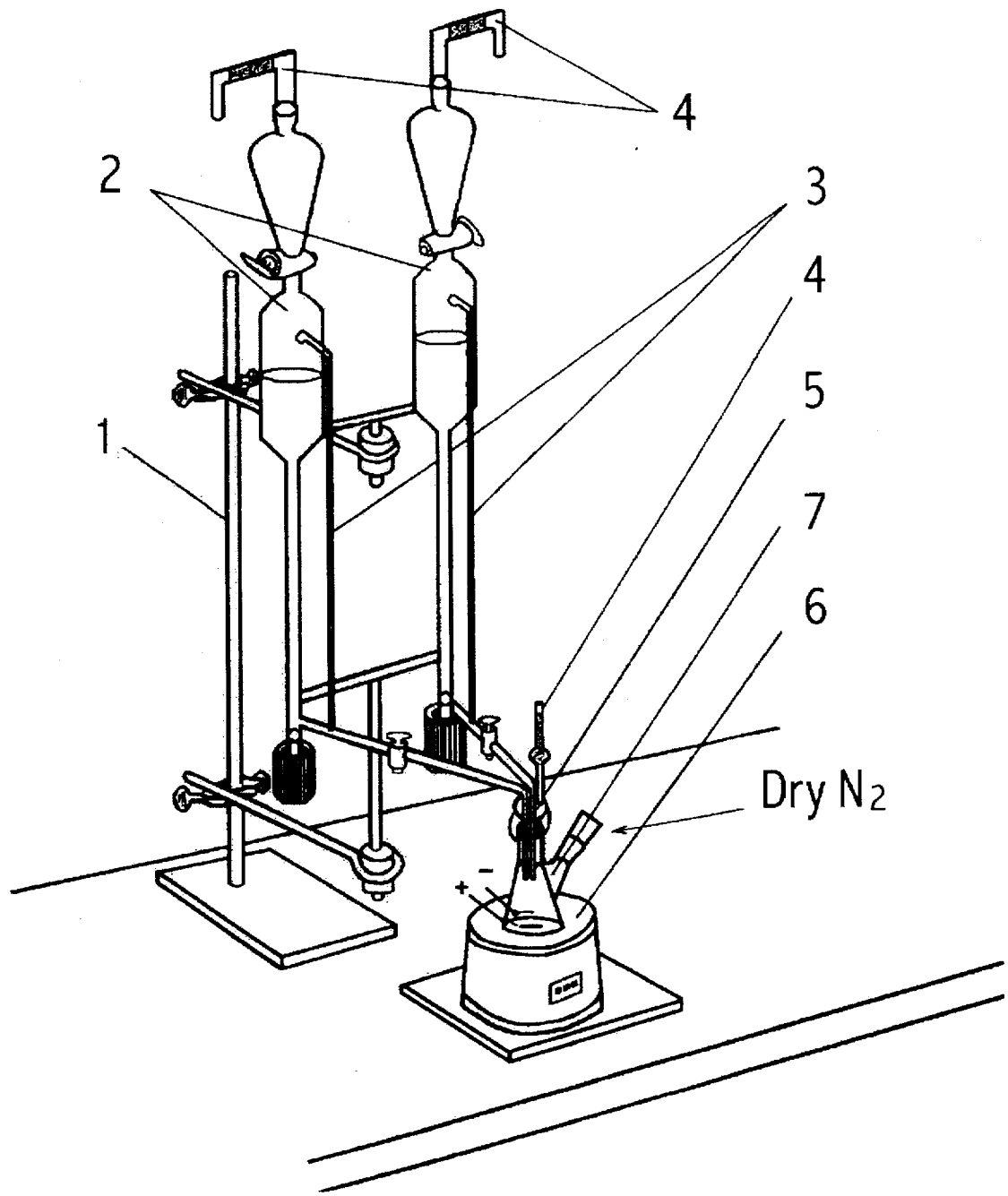

REAGENT FOR THE DETERMINATION OF WATER AMD ENE-DIOLS OR THIOLS

FIELD OF INVENTION

The present invention concerns the methods of quantitative water content determination in chemicals, drugs, foodstuffs, cosmetic products and other objects. The invention provides, in particular, the amenable water content determination in a sample inaccessible for K. Fischer titration due to its interaction with a sample matrix containing ene-diols or tiols.

BACKGROUND OF THE INVENTION

Ene-diols (like vitamin C and its preparations) and thiol derivatives are used in the pharmaceutical, petrochemical, perfumery and food industries as antidots, pesticides and stabilizers of polymerization and others.

Ene-diols and thiols through auto-oxidation, or oxidation in the presence of a base by oxygen or iodine form diketons and sulfide derivatives (Advanced Organic Chemistry, 3rd, Ed. J. March, Wiley, NY(1985), p.1092). Ascorbic acid in drugs can be determined by iodometric method (USP 1995, pp.130, 1414, 2215). There are no general iodometric methods for all the thiols since reaction stoichiometry between SH-group and iodine depends on their structure (N. D. Cheronis and T. S. Ma, Organic Functional Group Analysis by Micro and Semimicro Methods, Wiley, NY(1964), p.323). The standard techniques for water determination "loss on drying" at high temperature, azeotropic toluene distillation and direct or residual titration by K. Fischer reagent (KFR) (USP 1995, pp.1801, 1840, 1842) are unsuitable for the evaluation of the moisture of ascorbic acid and thiols.

The "loss on drying" technique up to 60° C. with $P_2O_5$ or without it, which is recommended for the analysis of ascorbic acid (USP 1995, pp. 1414, 1164) and SH-group compounds (USP 1995, pp.960, 1162,1164) is labor-consuming and protracted and does not guarantee the complete dehydration of drugs, containing gluing components, fillers and stabilizers like polymers, polysaccharides, organic and inorganic salts possessing relatively high heats of absorption (F. B. Sherman, Talanta, 301(1983), p.705; J. T. Carstensen et al., Drug Dev. and Ind. Pharm., 19(1993), p.195). The K. Fischer reaction takes place quickly and quantitatively in excess of methanol, when value range from 5.5–8.0 (J. C. Verhoev, E. Barendrecht, J. Electroanal. Chem., 75(1977), p.705). For maintaining stoichiometry of the K. Fischer reaction, i.e. the $H_2O:J_2=1:1$ ratio independent of reagent content, the content of methanol in the reagent must be 50–60% (F. B. Sherman, Talanta, 27(1980), p.1067). By the direct titration of ascorbic acid and thiol by KFR one obtains over-rated data since the K. Fischer reagent is an iodometric titration in non-aqueous media, while is simultaneously participating both in the reaction with $SO_2$ and water and in the reaction of ene-diol or SH-group.

While analyzing ascorbic acid, alkyl- and arylthiols, thiophenols, thionaphthalenes and some other thiols, the amount of KFR corresponds to the total water and analyzed assay contents (J. Mitchell Jr. and D. M. Smith, Aquametry, 2nd Ed. Part 3, Wiley, NY (1980), pp 45, 310, 361). The techniques for the determination of moisture in ascorbic acid and thiols by KFR are based on their preliminary oxidation with non-aqueous iodine solution. The oxidation of ascorbic acid or thiols by iodine is conducted in the conditions of basic catalysis, usually in presence of pyridine. Another way for neutralization of the assay influence on the KFR titration is the masking of the thiol with a double bond of olefines, acrylonitrile or N-ethylmaleimide. When the thiols are neutralized by olefines, boron fluoride-ether or $BF_3$ in acetic acid are used as catalysts (see above-mentioned J. Mitchell Jr. and D. M. Smith, Aquametry, p.361; H. J. Francis and D. D. Perrsing, Talanta, 25 (1978), p.282). These techniques based on highly toxic compounds such as $BF_3$, acrylonitrile or N-ethylmaleimide can be used while determining the small quantity of water, for instance, in normal straight-chain thiols from $C_2$ to $C_{12}$ in low molecular-weight mercapto acids and their esters.

The precursors of our invention are the reagents and techniques based on the KFR for volumetric titration consisting of two components: (1) Solvent $SO_2$ and organic base mixture usually in methanol or cellosolve and (2) Titrant-iodine in the same mixtures. When adding the Titrant to the Solvent the KFR is formed since these solutions contain all the components necessary for the K. Fischer reaction (A. Johansson, Anal. Chem., 28 (1956), p. 1166; E. Scholz, F.Z. Anal. Chem., 305 (1981), p.416; B. Just and W. Pawlowski, Chemia, Analyt., Poland, 30 (1985) p.803).

In accordance with these research works the ascorbic acid or thiol sample is dissolved in the methanol-pyridine mixture (Johansson; Jast and Pawlowski) or formamide (Scholz) and is neutralized with the Titrant. Then the Solvent is added and the total water content in the sample, solvents, in the Solvent and in the Titrant is determined. A second sample in the same solvent mixture considered blank is neutralized with the Titrant. The sample moisture is calculated according to the difference in the two titrations: Titrant volume during the blank and neutralization of the assay. For analysing of dried fruits, ascorbic acid and water are first extracted by methanol (B. Just and W. Pawlowski). In an aliquote of the extract ascorbic acid and water are titrated by KFR while ascorbic acid only is titrated by iodine in the methanol-pyridine mixture. The moisture content of the dried fruits is calculated according to the difference of these titrations.

The drawbacks of the reagents and technique-precursors (see Johansson, 1956; Scholz, 1981; Just and Pawlowski, 1985)

A. The reagents are toxic.
B. For determining water and assay according to the difference titration of by KFR and the Titrant two samples are used.
C. The water content in the Titrant, used for neutralizing the assay, is not estimated.
D. The oxidation of thiols by the Titrant without the basic catalyst, that limits the possibilities of the techniques, is conducted.
E. With the introduction of the Solvent after the neutralization of the assay by the Titrant, the system air-tightness is violated.

NOVEL REAGENTS AND TECHNIQUE

1. General description

The present invention relates to a novel set of reagents for the simultaneous iodometric determination of water and ene-diols or thiols in non-aqueous media. They contain iodine, iodide, non-toxic organic or inorganic base and a system of polar non-aqueous solvents. With the help of these reagents it is possible to perform the consecutive quantitative determination of ene-diols or thiols without a preliminary dissolution (1st titration) and of water content by KFR (2nd titration) in one sample using a double burette for titrations and electrometric location of the end point in both titrations (FIG. 1) (or a multistage titroprocessor). The solution formed after the 1st titration is a medium for water content determination by KFR.

We have shown on numerous examples, i.e. on 2-mercaptopyrimidine, mercapto-1-methylimidazole, 2-mercaptobenzoxazole and 2-mercaptobenzimidazole that their oxidation by Hydranal-Titrant (Reidel-de Haen) is not quantitative in formamide, N,N-dimethylformamid (DMF), and dimethyl sulfoxide (DMSO) or their mixtures with methanol, if a base is absent. The titrations of ascorbic acid or 2-mercaptopyrimidine by the iodine solution in presence of 0.1–0.2 mol/L diethanolamine (DEA), thriethanoleamine (TEA) or imidazole are also incorrect and "an unstable" end point titration is observed. To obtain stable 0.08–0.15 N iodine solutions in presence of 0.1–0.2 mol/L DEA or TEA it is necessary to use 2–2.5-fold excess of iodine content. Such reagent oxidizes quickly and quantitatively ene-diol (ascorbic acid) and thiol (2-mercaptopyrimidine) groups only in the presence of urea (Reagent 2, p.7). The reagent based on urea only (without DEA or TEA, Reagent 1, p.7) oxidizes also quantitatively ascorbic acid and 2-mercaptopyrimidine, but in this case the reaction for determination of water at the beginning of the titration is slow and accelerates with the addition of the KFR. This fact can be explained by the low pH value of the media following the titration of such reagent. A major factor in the quantitative analysis of the ene-diols and thiols contained in the complex samples is the choice of the non-aqueous solvent system that ensures the quantitative extraction and dissolution of the assay and reaction products-diketones, disulfides or sulfonyliodides. For example, mercaptopurines and mercaptopyrimidines are dissolved badly in methanol and therefore for the preparations of reagents the methanol mixtures with DMF and DMSO, DMF or formamide were used.

The use of sample semimicroweights (20–60 mg) in the analysis increases the possibility of the quantitative extraction of ene-diols or thiols during the titration on account of the "dilution effect". In this analysis the reagents fulfill a double role—that of a titrant for an assay and that of media for water content determination by the KFR.

2. Reagents

With the aim of excluding a blank, the present invention presupposes the introduction of one sample into a flask (FIG. 1) and the matrix is titrated by the reagent without any solvents (a sample can be introduced in a minimum reagent volume, if the approximate content of ene-diols or thiols is known). The reagents are prepared from dried components, but even so they have a residual humidity around 0.02–0.05%. It is impossible to measure directly the water content by the KFR in the iodine containing reagents, therefore these reagents should be standardized against iodine and water. For the analysis of samples with low concentrations of ene-diols and thiols, larger sample weight or dilute reagents should be used.

The following Examples illustrate the invention

The given recipes are calculated for preparation of one liter of the solution. While it is expedient to prepare and keep concentrated reagents with titres 0.4–0.6 mol/L it is better to use for work the diluted ones, depending on the analytical aim set.

Reagent 1

0.1 mol iodine, 0.075–0.13 mol tetramethyammonium iodide and 1–2 mols urea are dissolved in the mixture of methanol—DMF-DMSO (4:1:0.5) vol.

Reagent 2

0.15 mol iodine, 0.17 mol tetramethylammonium iodide, 0.1 mol DEA and 1 mol urea are dissolved in the mixture of DMF-methanol (1:3) vol.

Reagent 3

3 0.18 mol iodine, 0.24 mol potassium iodide, 0.1 mol DEA and 1 mol urea are dissolved in the mixture of DMF-methanol (1:3) vol.

Reagent 4

0.15 iodine, 0.25 mol potassium iodide, 0.1 mol TEA and 1 mol urea are dissolved in the mixture DMF-methanol (1:3) vol.

Reagent 5

0.18 mol iodine, 0.24 mol potassium iodide, 0.1 mol DEA and 1 mol urea are dissolved in the mixture formamide-methanol (1:3) vol.

Reagent 6

0.15 mol iodine, 0.25 mol potassium iodide, 0.1 mol TEA and 1 mol urea are dissolved in the mixture formamide-methanol (1:3) vol.

Reagent 7

0.05–0.1 mol iodine, 0.07–0.13 mol potassium iodide and 0.2–0.3 mol sodium acetate are dissolved in the mixture formamide-methanol or DMF-methanol (1:3) vol.

According to Reagents 1–7 recipes tetramethylammonium iodide, potassium iodide and sodium acetate are dried up to 120° C.; urea is maintained in a dessiccator over anhydron for three days. The solvents—DMF, formamide and DMSO and the bases—DEA and TEA are distilled at reduced pressure in the presence of dry argon; DMF is distilled over $P_2O_5$. The distilled solvents are maintained over dehydrated molecular sieves 3 A regenerated at 360° C. and vacuum. Dry methanol (0.005% water, Merck) and the iodine (assay 99.8%, Merck) are used. Anhydrous tin (II) chloride (Merck) is dried at 150° C. and used for the determination of water content in the reagents.

Reagents 1–7 are maintained for two days. The titres of prepared Reagents 1–7 were 0.08–0.15 N iodine. The reagents are stored in air-tight containers made of amber-glass. The KFR is prepared from Hydranal-Composite 5 (Riadel-de Haen) which is diluted 4–7 times with the mixture of dry methanol and Hydronal-Solvent (in ratio 3:1). These solutions have titres of 0.5–1.3 mg $H_2O$/Ml.

The technique for the simultaneous determination of water and ene-diols or thiols by Novel Reagents and K. Fischer titration The dried flask with Pt-electrodes is connected to a double burette, then the air is displaced from the flask by a dry inert gas and via the side pipe a sample weighing 20–60 mg contained in a 0.5–1 ml Teflon (trademark of E. I. Du Pont de Nemours & Co. for tetrafluoroethylene) bottle is introduced (FIG. 1). The ene-diol or thiol is titrated by the reagent. The equivalent point is located by a dead-stop end-point method with the help of pH Meter, Radiometer, under polarizing voltage 280 mV (1st titration). The reagent volume spent for the assay is used for the calculation of water contents in a sample (see Eq. 1). Then the water in the solution that is formed after first titration by the reagent is titrated by the KFR (second titration). The equivalent point with the KFR titration is located also by the dead-stop end-point method. With the aim of increasing the sensitivity of the equivalent point location during the titrations an additional resistance of 20 k$\Omega$ is introduced into the electrometric scheme. (The change of the intensity of current at the equivalent point is equal to only 30 μA). An analytical balance with uncertainty ±0.01 mg (Mettler AE 163, Switzeland) is used.

It is impossible to air-tighten ideally the titration flask from the atmospheric humidity and therefore while performing the KFR titration the equivalent point is set according to the position of pH meter indicator meeting the minimum potential value. The value should be stable with the stirrer working for about 1 min, that corresponds to the minimal iodine excess at the equivalent point. The titres of reagents on iodine and water are established according to a standard sodium thiosulfate solution and anhydrous tin (II) chloride (30–50 mg) correspondingly. The titre of the KFR established according to known water amounts (3–5 mg) or sodium tartrate dihydrate (20–40 mg) correspondingly. The reagents and KFR titres are checked twice weekly.

Calculation of the ene-diol or thiol and water contents in a sample

The ene-diol or thiol contents are calculated as usual in titrometry, and the water contents are calculated from Eqs. (1) and (2):

$$C_W = (V_{KFR} - fV_R) T_{KFR} 100/m \quad (1)$$

where $C_w$ is the concentration of water, (%);

$V_{KFR}$ is the volume of the KFR spent for titration of the solution formed after the first titration, (mL);

f is a factor that corresponds to the volume of the KFR spend for titration of water in 1 mL of the novel reagent (mL).

$V_R$ is the volume of the Reagent spent for titration of the sample (mL);

$T_{KFR}$ is the titre of the KFR (mg $H_2O$ $mL^{-1}$);

m is the mass of the sample, (mg).

The value of factor f is calculated from two consecutive titrations of the same dry $SnCl_2$ sample by the reagent and then by KFR:

$$f = V°_{KFR}/V°_R \quad (2)$$

where $V°_R$ is the volume (mL) of the reagent spend for titration of the dry $SnCl_2$ sample (first titration);

$V°_{KFR}$—is the volume of the KFR spend for titration of the solution formed after the first titration (ml KFR).

Precision and accuracy of results
Objects for study

We prepared artificial mixtures of L(+)ascorbic acid (Merck) or 2-mercapto-pyrimidine (Aldrich) with sodium tartrate dihydrate (GR, Merck) (Table 1).

TABLE 1

Initial substances for preparation of artificial mixtures

| Substance | Ene-diols or thiols, (%) | Water, (%) |
| --- | --- | --- |
| Ascorbic acid | 99.3 ± 0.8 | 0.34 ± 0.06 |
| 2-Mercaptopyrimidine | 97.5 ± 0.3 | 0.33 ± 0.02 |
| Sodium tartrate dihydrate | — | 15.66 ± 0.08 |

Ascorbic acid and 2-mercaptopyrimidine are determined iodometrically. The titration of 2-mercaptopyrimidine is performed in iso-propanol since thiol and disulfide can be dissolved in it. The water content in sodium tartrate dihydrate is determined for direct K. Fischer titration, while the water content in ascorbic acid and 2-mercaptopyrimidine is calculated according to the difference between the KFR spending for water content and assay titration and for the iodometric titration of the assay only. This technique for the determination of water content in the initial substance was used because the standard techniques are not suitable for this purpose (see p.2). Results of determinations (average from 5 replicates ± standard deviation) are shown in Table 1. The data correspond to Certificate of Guarantee of Merck (ascorbic acid, GR) and Aldrich (2-mercaptopyrimidine).

Precise weights of the components are introduced into glass bottles, then mixed, and small portions of the obtained mixtures are additionally triturated in a china mortar and thoroughly mixed once again. With this method of mixture preparation there are inevitable partial component losses. Therefore the true value of assay and water in these specified artificial mixtures have been defined with the help of accepted double-titration technique, using the KFR and iodometry. The results of these determinations (from 5 replicates), taken as "true" results, ($X_{tr}$), are given in Table 2 and 3.

Precision (in terms of repeatability and reproducibility) and accuracy of the results of water determination and assay were evaluated from the data shown in Tables 2 and 3. These data were obtained in different days by the novel technique of analysis for the model mixtures. In examples 1–3 Reagent 2 was used, in examples 5–7 —Reagent 3, in examples 4 and 8 Reagent 4.

The repeatability was evaluated as an average relative standard deviation, $S_1$(% rel.), between the replicates for a given mixture, and the reproducibility was evaluated as the relative standard deviation, $S_2$(% rel.), between the average results of determination for a given mixture per day.

From Table 2 it can be seen that for water determination $S_1 < 5\%$ rel. and $S_2 < 7\%$ rel. and from Table 3, for ascorbic acid or 2-mercaptopyrimidine determination, $S_1 < 2\%$ rel. and $S_2 < 3\%$ rel. These values are acceptable for a titration technique.

The accuracy was evaluated as the bias B of the general average result ($X_{av}$) from $X_{tr}$ calculated as relative percentage.

The values of $X_{av}$ were systematically less than $X_{tr}$ (B<O) for ascorbic acid or 2-mercaptopyrimidine probably because of the differences in conditions for the determination of reagents titres and for sample analysis. The reagent titres were established against 0.1 N sodium thiosulphate solution, i,e. in an aqueous solution, while the analysis was performed in a non-aqueous medium with a water content more than one order of magnitide lower than the determined values of the ascorbic acid or 2-mercaptopyrimidine content.

However, the accuracy of determination is sufficient for all analyses at the 99% level of confidence since all values of the bias are less than the critical values $t_{0.99} S_2$, where t is the coefficient of the Student's distribution for 5−2=3 degrees of freedom. From Tables 2 and 3 it also follows that the reagents completely neutralize ascorbic acid or 2-mercaptopyrimidine, since they have no influence on the titration of water by KFR: the bias values in Table 2 have positive as well as negative values.

Advantages of the Novel Reagents and their use with the double burette for water and ene-diols or thiols determination A. The Reagents are non-toxic.
B. While determining water and ene-diol or thiol contents by the novel reagents and the KFR a single sample is sufficient.
C. The determination of water and ene-diol or thiol is performed without a blank.

D. The ene-diol or thiol determination by the novel reagents is performed without the use of an extra solvent.

E. The methanol content of 50–60% in the reagents makes it possible to use any KFR modification for ene-diols or thiols moisture determination.

BRIEF DESCRIPTION OF THE FIGURE

The invention is illustrated with reference to FIG. 1, which is a schematical drawing, not according to scale, of a double burette for the simultaneous determination of water and ene-diols or thiols, wherein 1 designates a stand, 2 designates reservoirs, 3 designates a 5ml burette graduated in 0.01 ml divisions, 4 designates a tube for protection from atmospheric moisture with silica gel, blue and anhydron; 5 designates a titration flask with Pt-electrodes for electrometric location of the end point, 6 is a magnetic stirrer and 7 a side pipe for a liquid, gaseous or solid sample.

TABLE 2

The results of the water determination in the model mixtures by the novel technique

| Example Number | "True" conc., % | Replicate Number | Day/Result of determ., % | | | | | $S_1$ % | $S_2$ % | B, % | $t(0.99)S_2$ % |
|---|---|---|---|---|---|---|---|---|---|---|---|
| | | | 1 | 2 | 3 | 4 | 5 | | | | |
| 1 | 1.85 | 1 | 1.87 | 1.83 | 1.72 | 1.76 | 1.82 | 4.17 | 6.37 | 1.03 | 37.21 |
| Asc. acid + | | 2 | 2.15 | 1.9 | 1.9 | 1.79 | 1.68 | | | | |
| tartrate | | 3 | 2.25 | 1.94 | 1.78 | 1.9 | 1.75 | | | | |
| 2 | 4.68 | 1 | 5.29 | 5.13 | 4.8 | 5.03 | 4.87 | 2.00 | 2.20 | 7.12 | 12.87 |
| Asc. acid + | | 2 | 4.93 | 5.26 | 5 | 5.09 | 5.01 | | | | |
| tartrate | | 3 | 5.19 | 5.07 | 5.06 | 5.13 | 4.72 | | | | |
| 3 | 9.92 | 1 | 10.58 | 9.94 | 10.4 | 9.53 | 9.45 | 1.40 | 3.24 | 0.36 | 18.91 |
| Asc. acid + | | 2 | 9.92 | 9.83 | 10.29 | 9.92 | 9.7 | | | | |
| tartrate | | 3 | 10.56 | 9.89 | 10.22 | 9.6 | 9.51 | | | | |
| 4 | 4.68 | 1 | 4.66 | 4.55 | 4.74 | 4.58 | 4.83 | 1.52 | 1.78 | −1.02 | 10.42 |
| Asc. acid + | | 2 | 4.6 | 4.48 | 4.81 | 4.69 | 4.63 | | | | |
| tartrate | | 3 | 4.5 | 4.45 | 4.59 | 4.73 | 4.65 | | | | |
| 5 | 1.69 | 1 | 1.6 | 1.64 | 1.79 | 1.62 | 1.56 | 2.00 | 3.76 | −2.97 | 21.98 |
| 2-MP + | | 2 | 1.55 | 1.62 | 1.69 | 1.67 | 1.64 | | | | |
| tartrate | | 3 | 1.58 | 1.58 | 1.76 | 1.73 | 1.59 | | | | |
| 6 | 4.75 | 1 | 4.97 | 4.9 | 5.04 | 4.92 | 4.97 | 1.32 | 1.91 | 3.48 | 11.14 |
| 2-MP + | | 2 | 4.6 | 5.02 | 5.08 | 4.94 | 4.9 | | | | |
| tartrate | | 3 | 4.72 | 4.8 | 5.04 | 4.91 | 5.01 | | | | |
| 7 | 9.92 | 1 | 9.7 | 9.85 | 9.64 | 9.78 | 9.82 | 0.41 | 0.66 | −1.39 | 3.88 |
| 2-MP + | | 2 | 9.75 | 9.8 | 9.76 | 9.83 | 9.88 | | | | |
| tartrate | | 3 | 9.74 | 9.73 | 9.69 | 9.85 | 9.94 | | | | |
| 8 | 4.75 | 1 | 4.85 | 4.72 | 4.86 | 4.82 | 4.79 | 1.19 | 1.49 | 0.78 | 8.69 |
| 2-MP + | | 2 | 4.81 | 4.63 | 4.96 | 4.77 | 4.68 | | | | |
| tartrate | | 3 | 4.76 | 4.62 | 4.8 | 4.78 | 4.96 | | | | |

TABLE 3

The results of the assay determination in the model mixtures by the novel technique

| Example Number | "True" conc., % | Replicate Number | Day/Result of determ., % | | | | | $S_1$ % | $S_2$ % | B, % | $t(0.99)S_2$ % |
|---|---|---|---|---|---|---|---|---|---|---|---|
| | | | 1 | 2 | 3 | 4 | 5 | | | | |
| 1 | 87.79 | 1 | 85.9 | 85.16 | 85.44 | 86.82 | 85.32 | 0.80 | 0.63 | −1.98 | 3.65 |
| Asc. acid + | | 2 | 85.77 | 86.4 | 86.19 | 85.53 | 86.08 | | | | |
| tartrate | | 3 | 84.89 | 89.53 | 85.99 | 86.53 | 85.69 | | | | |
| 2 | 69.24 | 1 | 63.69 | 64.12 | 64.83 | 64.42 | 66.97 | 1.30 | 1.57 | −6.45 | 9.18 |
| Asc. acid + | | 2 | 64.09 | 63.33 | 65.03 | 66.46 | 69.34 | | | | |
| tartrate | | 3 | 63.62 | 65.35 | 65.32 | 65.1 | 64.01 | | | | |
| 3 | 36.41 | 1 | 34.06 | 35.48 | 35.71 | 34.62 | 36.01 | 1.04 | 1.18 | −3.58 | 6.86 |
| Asc. acid + | | 2 | 33.93 | 35.16 | 35.16 | 35.33 | 35.59 | | | | |
| tartrate | | 3 | 35.12 | 35.01 | 35.1 | 35.81 | 35.19 | | | | |
| 4 | 69.24 | 1 | 64.46 | 62.48 | 65.35 | 66.33 | 67.45 | 0.63 | 2.17 | −6.69 | 12.66 |
| Asc. acid + | | 2 | 63.96 | 63.45 | 64.86 | 65.47 | 66.69 | | | | |
| tartrate | | 3 | 63.48 | 62.79 | 64.16 | 65.91 | 66.59 | | | | |
| 5 | 89.75 | 1 | 85.96 | 86.91 | 85.72 | 87.2 | 85.95 | 0.40 | 0.85 | −3.97 | 4.97 |
| 2-MP + | | 2 | 86.65 | 87.25 | 84.64 | 87.41 | 86.56 | | | | |
| tartrate | | 3 | 85.13 | 87.13 | 85.23 | 86.8 | 86.26 | | | | |
| 6 | 70.46 | 1 | 67.89 | 66.68 | 65.46 | 65.08 | 65.51 | 0.67 | 1.84 | −6.35 | 10.76 |
| 2-MP + | | 2 | 67.08 | 66.73 | 65.69 | 64.65 | 65.31 | | | | |
| tartrate | | 3 | 69.46 | 68.13 | 65.41 | 64.74 | 65.95 | | | | |
| 7 | 37.87 | 1 | 36.42 | 36.08 | 36.27 | 36.34 | 38.22 | 0.74 | 2.44 | −3.73 | 14.25 |
| 2-MP + | | 2 | 36.31 | 35.64 | 35.55 | 36.7 | 38.62 | | | | |
| tartrate | | 3 | 35.93 | 35.74 | 35.45 | 36.75 | 37.72 | | | | |
| 8 | 70.46 | 1 | 69.01 | 67.62 | 67.77 | 68.02 | 68.64 | 0.61 | 0.87 | −3.45 | 5.08 |
| 2-MP + | | 2 | 68.47 | 66.93 | 67.41 | 69 | 67.78 | | | | |
| tartrate | | 3 | 68.89 | 66.69 | 68.93 | 68.74 | 67.79 | | | | |

We claim:

1. A reagent for a quantitative determination of water and one of ene-diols and thiols in a test sample, comprising iodine and an organic or an inorganic iodide, and a base, in a non-aqueous solvent.

2. The reagent according to claim 1, wherein said iodide comprises tetramethylammonium iodide, said base comprises urea, and said in a solvent comprises a mixture of methanol, formamide or N,N-dimethylformamide, and dimethylsulfoxide in a ratio of 4:1:0.5 by volume.

3. The reagent according to claim 1, wherein said iodide comprises tetramethylammonium iodide, said base comprises urea and diethanolamine, and said solvent comprises a mixture of methanol and, formamide or N,N-dimethylformamide, in a ratio of 3:1 by volume.

4. The reagent according to claim 1, wherein said iodide comprises potassium iodide, said base comprises urea and diethanolamine, and said solvent comprises a mixture of methanol and, formamide or N,N-dimethylformamide, in a ratio of 3:1 by volume.

5. The reagent according to claim 1, wherein said iodide comprises potassium iodide, said base comprises urea and triethanolamine, and said solvent comprises a mixture of methanol and, formamide or N,N-dimethylformamide, in a ratio of 3:1 by volume.

6. The reagent according to claim 1, wherein said iodide comprises potassium iodide, said base comprises sodium acetate and said solvent comprises a mixture of methanol and, formamide or N,N-dimethylformamide, in a ratio of 3:1 by volume.

* * * * *